(12) United States Patent
Khan (10) Patent No.: US 8,304,579 B2
(45) Date of Patent: Nov. 6, 2012

(54) BORONIC ACID ARYL ANALOGS

(75) Inventor: Saeed R. Khan, Owing Mills, MD (US)

(73) Assignee: Johns Hopkins University, Baltimore, MD (US)

( * ) Notice: Subject to any disclaimer, the term of this patent is extended or adjusted under 35 U.S.C. 154(b) by 0 days.

(21) Appl. No.: 12/940,439

(22) Filed: Nov. 5, 2010

(65) Prior Publication Data

US 2011/0105431 A1 May 5, 2011

Related U.S. Application Data

(62) Division of application No. 10/596,751, filed as application No. PCT/US2004/043114 on Dec. 21, 2004, now Pat. No. 7,829,742.

(60) Provisional application No. 60/531,765, filed on Dec. 22, 2003.

(51) Int. Cl.
C07F 5/02 (2006.01)
A01N 55/08 (2006.01)

(52) U.S. Cl. .............................................. 568/6; 514/64

(58) Field of Classification Search ......... 568/6; 514/64
See application file for complete search history.

(56) References Cited

FOREIGN PATENT DOCUMENTS

| EP | 0 947 511 A1 | 10/1999 |
|---|---|---|
| WO | WO 91/17749 A1 | 11/1991 |
| WO | WO 03/106384 A2 | 12/2003 |

OTHER PUBLICATIONS

Freshney, Culture of Animal Cells, A Manual of Basic Technique, Alan R. Liss, Inc., 1983, New York, p. 4.*
Simeone in Cecil Textbook of Medicine, 20th ed. J.C. Bennett. Philadelphia: WB Saunders Co., 1996. Published as 1 volume.*
Achanta et al. Mol Pharmacol 70:426-433, 2006.*
Bouget et al., "Hydrazino-Aza and N-Azapeptoids with Therapeutic Potential as Anticancer Agents," Bioorg. Med. Chem. (2003), 11:4881-4889.
Catlin and Snyder, "Preparation and Reactions of o-(Cyanomethyl)benzeneboronic Acid," J. Organic Chem. (1969), 34(6):1660-1663.
Catlin and Snyder, "Synthesis, Reactions, and Mass Spectral Studies of Some Cyclic Amine-Boranes and their Catechol Derivatives," J. Organic Chem. (1969), 34(6): 1664-1668.
DiCesare and Lakowicz, "Chalcone-Analogue Fluorescent Prfobes for Saccharides Signaling Using the Boronic Acid Group," Tetrahedron Lett. (2002), 43:2615-2618, Pergamon Press.
Dinkova-Kostova, "Potency of Michael Reaction Acceptors as Inducers of Enzymes that Protect against Carcinogenesis Depends on their Reactivity with Sulfhydryl Groups," PNAS (2001) 98(6):3404-3409.
Falck et al., "Bromo-Boronolactonization of Olefins," J. Org. Chem. (2001), 66:7148-7150, American Chemical Society.
Falck et al., "Homocoupling of Alkyl-, Alkenyl-, and Arylboronic Acids," Tetrahedron Lett. (2002), 43:8149-8151, Pergamon Press.
Fu and Snieckus, "Connections to the Directed Ortho Metalation Strategy. Pd(O)-Catalyzed Cross Coupling of Aryl Boronic Acids with Aryl Triflates," Tetrahedron Lett. (1990), 31(12):1665-1668, Pergamon Press.
Jiang et al., "Furoyl and Benzofuroyl Pyrroloquinolones as Potent and Selective PDE5 Inhibitors for Treatment of Erectile Dysfunction," J. Med. Chem. (2003), 46:441-444, American Chemical Society.
Kobayashi et al., "Zinc Borates: Functionalized Hard Nucleophiles for Coupling Reactions with Secondary Allylic Acetates," Eur. J. Org. Chem. (2000), 3825-3834, Wiley-VCH Verlag GmbH.
Kumar et al., "Design, Synthesis, and Evaluation of Novel Boronic-Chalcone Derivatives as Antitumor Agents," J. Med. Chem. (2003), 46:2813-2815, American Chemical Society.
Meng et al., "Discovery of Novel Heteroaryl-Substituted Chalcones as Inhibitors of TNF-α-Induced VCAM-1 Expression," Bioorg. Med. Chem Lett. (2004), 14:1513-1517, Elsevier Ltd.
Nan and Yang, "Nickel-Catalyzed Cross-Couplings of Cyclohexenyl Phosphate and Arylboronic Acids," Tetrahedron Lett. (1999), 40:3321-3324.
Roberts et al., "Pluripotential Amino Acids I. (L)-p-Dihydroxyborylphenylalanine (L-Bph) as a Precursor of L-Phe and L-Tyr Containing Peptides; Specific Tritiation of L-Phe-Containing Peptides at a Final Step in Synthesis," Tetrahedron Lett. (1980), 21:3435-3438, Pergamon Press Ltd.
Serafin and Makosza, "Arylboronic Compounds-VIII. Some Reactions of Hydroxy and Carboxyphenylboronic Acids," Tetrahedron (1963), 19:821-826, Pergamon Press Ltd.
Skowrouska-Serafin and Makosza, "Database Beilstein, Beilstein Crossfire Institut zur Foerderung der Dhemischen Wissenschaften," Citation No. 2508506, BRN 488408 1991, XP002327019, Rocz. Chem. (1961), 35:359-362.
Snyder et al., "Synthesis of Aromatic Boronic Acids. Aldehydo Boronic Acids and a Boronic Acid Analog of Tyrosine," J. Am. Chem. Soc. (1958), 80:835-838.
Strachan et al., "The Preparation of Some 1,7b-disubstituted cyclopropa[c]isoquinolines via Nitrile Ylide Cyclisations and their Rearrangement to 2-benzaaepines and 4-alkenyl-1,4-dihydroisoquinolines," J. Chem. Soc., Perkin Trans. 1 (1998), 13:807-812.
Yang et al., "Boronic Acid Compounds as Potential Pharmaceutical Agents," Med. Res. Rev. (2003), 23(3):346-368.

* cited by examiner

Primary Examiner — Nizal Chandrakumar
(74) Attorney, Agent, or Firm — DLA Piper LLP (US)

(57) ABSTRACT

The present invention relates to novel boronic acid aryl derivatives which are useful as antitumor/anticancer agents. The present compounds, which are inexpensive to synthesize, exhibit unexpectedly good inhibitors of the growth of human breast cancer cells. The present invention also relates to the use of the novel boronic acid aryl derivatives to treat cancer. The invention also provides pharmaceutical compositions comprising the inhibitors of the invention and methods of utilizing the inhibitors and pharmaceutical compositions in the treatment and prevention of cancer.

3 Claims, 4 Drawing Sheets

BORONIC ACID ARYL ANALOGS

CROSS-REFERENCES TO RELATED APPLICATIONS

This is a divisional application of U.S. application Ser. No. 10/596,751 filed Oct. 18, 2007, now issued as U.S. Pat. No. 7,829,742; which is a 35 USC §371 National Stage application of International Application No. PCT/US2004/043114 filed Dec. 21, 2004; which claims the benefit under 35 USC §119(e) to U.S. Application Ser. No. 60/531,765 filed Dec. 22, 2003, now expired. The disclosure of each of the prior applications is considered part of and is incorporated by reference in the disclosure of this application.

STATEMENT AS TO RIGHTS TO INVENTIONS MADE UNDER FEDERALLY SPONSORED RESEARCH AND DEVELOPMENT

This study was supported by FAMBRI to (S. R. K.) and had been assigned to Johns Hopkins University.

BACKGROUND OF THE INVENTION

1. Field of the Invention

This invention relates to novel boronic chalcone compounds and uses thereof. The compounds of this invention are particularly useful for the treatment of tumors and cancers.

2. Background Information

Throughout this application, various publications are referenced by author and date. The disclosures of these publications are hereby incorporated by reference in their entireties into this application in order to more fully describe the state of the art as known to those skilled therein as of the date of this invention described and claimed herein.

Breast cancer is expected to account for 203,500 new cancer cases and 39,600 deaths in 2002 (Jemal, A. et al., *CA Cancer J. Clin.*, 2002, 52, 23-47). Although major advances have been made in early detection, prevention, and treatment, the need for more effective therapy in the fight against late stage breast cancer continues. Currently there is no curative treatment for women with metastatic breast cancer once they have failed adjuvant therapies. New and effective cytotoxic agents with novel mechanisms of action are therefore urgently needed for the treatment of women with metastatic breast cancer. Hormone and chemotherapy, while of substantial palliative benefit, has had little impact on overall survival and the mortality rate from metastatic breast cancer. At the present time standard treatments for metastatic breast cancer include paclitaxel in combination with vinca alkaloids, etoposide, and other regimens that include agents such as anthacyclines, alkylating agents, antimetabolites, tamoxifen, and aromatase inhibitors (Chabner B A, Collins J M, Cancer chemotherapy principal and practice, pp 9-13, and 40-85. B. Lippincott Company, Philadelphia, 1990). The ultimate conclusion of these numerous studies over the last 50 years is that although these therapies provides significant palliative effect in the majority of with metastatic breast patients, it is likely to be curative. Although major advances have been made in early detection, prevention, and treatment of early disease, the need for more effective therapy in the fight against late stage breast cancer continues.

Recently the mouse double minute 2 (MDM2) oncogene has been suggested as a target for breast cancer therapy (Juven-Gershon, T. and Oren, M. *Mol. Med.*, 1999, 5, 71-83; Momand, J. et al., *Nucleic Acids Res.*, 1998, 26, 3453-3459). MDM2 is amplified or overexpressed in human breast cancer, and MDM2 levels are associated with poor prognosis of human breast cancer. The oncoprotein MDM2 inhibits the tumor suppressor protein p53 by binding to the p53 transactivation domain. The p53 gene is inactivated in human cancer either by mutations or by binding to oncogenic proteins such as MDM2 (Lane, D. P. and Hall, P. A., *Trends Biochem. Sci.*, 1997, 22, 372-374; Oliner, J. D. et al., *Nature*, 1992, 358, 80-83; Lozano, G.; Montes de Oca Luna, R., *Biochim. Biophys. Acta*, 1998, 1377, M55-M59; Wang, H. et al., *Clinical Cancer Res.*, 2001, 7, 3613-3624). In breast tumors, over expression of MDM2 inactivates an otherwise intact p53, disabling the genome integrity checkpoint and allowing cell cycle progression of defective cells (Boyd, M. T. et al., *J. Biol. Chem.*, 2000, 275, 31883-31890). Studies comparing MDM2 overexpression and p53 mutation concluded that these are mutually exclusive events, supporting the notion that the primary impact of MDM2 amplification in cancer cells is the inactivation of the endogenous wild-type p53 (Wang et al., supra). It has been shown recently that a peptide homologue of p53 is sufficient to induce p53-dependent death of cells overexpressing MDM2 (Wasylyk, C., et al., *Oncogene*, 1999, 18, 1921-1934). This result provides clear evidence that disruption of the p53/MDM2 complex might be effective in cancer therapy. It has been shown that MDM2 additionally has a role in tumor growth p53-independent mechanisms (Baker, S. J., et al., *Science*, 1990, 249, 912-915; Diller, L., et al., *Mol. Cell. Biol.*, 1990, 10, 5772-5781; Fakharzadeh, S. S., et al., *EMBO J.*, 1991, 10, 1565; Lundgren, K.; Montes de Oca Luna, R., et al., *Genes Dev.*, 1997, 11, 714-725; Zhang, R. and Wang, H., *Curr. Pharm. Des.*, 2000, 6, 393-416; Chabner, B. A. and Collins, J. M., *Cancer chemotherapy principal and practice*; Lippincott Williams & Wilkins Publishers Philadelphia, 1990; pp 9-13 and 40-85B).

Chalcones are a class of anticancer agents that have shown promising therapeutic efficacy for the management of human cancers. Chalcones, considered as the precursor of flavonoids and isoflavonoids, are abundant in edible plants. Chemically they comprise open-chain flavonoids in which the two aromatic rings are joined by a three-carbon $\alpha,\beta$-unsaturated carbonyl system. For example, chalcones have been observed to inhibit the proliferation of both established and primary ovarian cancer cells (De Vincenzo, R., et al, *Anticancer Drug Des.*, 1995, 10, 481-490). In vivo, chalcones have been demonstrated to be effective as antitumor agents in skin carcinogenesis (Statomi; Y., *Int. J. Cancer*, 1993, 55, 506-514; Yamamoto, S. et al, *Carcinogenesis*, 1991, 12, 317-323) and chemopreventive agents in several experimental models (Makita, H., et al., *Cancer Res.*, 1996, 56, 4904-4909; Rui, H., *J. Cell. Biochem.*, 1997, 67, 7-11; Wattenberg, L. W., et al., *Cancer Lett*, 1994, 83, 165-169). Recent studies have shown that these chalcones induce apoptosis in variety of cell types including breast cancers (Claude-Alain, C, et al., *Anticancer Res.*, 2001, 21, 3949-3956; WO 01/117988; WO 96/19209; U.S. Pat. No. 5,808,137; Maggiolini, M., et al., *J. Steroid Biochem. Mol. Biol.*, 2002, 82, 315-322; Stall, R., et al., *Biochemistry*, 2001, 40, 336-344; DiCesare, N. and Lakowicz, J. R., *Tetrahedron. Lett.*, 2002, 43, 2615-2618). Biochemical experiments have shown that these compounds could disrupt the MDM2/p53 protein complex, releasing p53 from both the p53/MDM2 and DNA-bound p53/MDM2 complexes (Stoll et al., supra).

Carboxylic chalcones have shown promising therapeutic efficacy for the management of human cancers (Daskiewicz, J. B., et al., *Tetrahedron Lett.* 1999, 40, 7095-7098; Devincenzo, R., et al., *Anti-Cancer Drug Des.* 1995, 10, 481-490). Previous studies (Stoll et al., supra; Kussie, P. H., et al., *Science*, 1996, 274, 948-953) on the binding modes of carboxylic acid analogs of chalcones with MDM2 revealed that the carboxylic acid group could be placed near the base of lysine-51 (K51), which is found in a salt bridge interaction with glutamic acid 25 (E25). It was presumed that the acid group of the chalcone forms a salt bridge with K51 and simultaneously breaks the salt bridge with E25 of the MDM2. However, carboxylic acid analogs of chalcone reported in the literature (Stoll et al., supra) are equally toxic to both normal and malignant breast epithelial cells. The toxicity to normal breast cells may be due to MDM2/p53 independent mechanisms. Therefore, a chalcone derivative that could strongly and irreversibly bind to and disrupt MDM2 protein complexes may be selectively toxic to MDM2 overexpressing breast cancer cells.

Boronic acids are Lewis acids and isosteres of carboxylic acid. The pKa's of boronic acids are about 9-10, and therefore at physiological pH boronic acids remain unionized (Tongcharoensirikul, P., et al., *Abstracts of Papers*, 222nd ACS national meeting, Chicago, Ill., August 26-30; American chemical society, Washington, D.C., 2001; MEDI-224). Thus, a coordinate covalent bond (boron-nitrogen) can be formed between a electron deficient boronic acid moiety and electron donating amino group, which may strongly enhance binding of boronic-chalcones with the lysine 51 of MDM2 at neutral pH when compared to the corresponding carboxylic acid analog of chalcones.

Boronic chalcone analogs have been previously described. These compounds have been used as fluorescent probes that may be useful for detection of fluorides (DiCesare, N. and Lakowicz, J. R., supra) and saccharides such as glucose that may be applicable to the design of biosensors for diabetes (DiCesare, N. and Lakowicz, J. R., supra). However, prior to this invention no investigations into the anticancer activity of boronic-chalcones on different cancer cell lines have been reported.

SUMMARY OF THE INVENTION

Surprisingly, it has now been found that certain novel chalcones derivatives, in particular boronic chalcone derivatives, possess antiproliferative activity on cancer cells at micromolar concentrations. Accordingly, this invention provides the design and synthesis of novel boronic chalcone derivatives, and pharmaceutical compositions containing these compounds. Several the compounds described herein were observed to have high activity in the breast cancer cell lines tested and has been shown to be 6-9 fold less toxic to normal MCF-12A cell lines compared to normal breast epithelial cell lines. The novel boronic chalcone analogs disclosed herein should overcome the limiting lack of specificity of carboxylic acid analogs of chalcones.

The present invention further investigates the potential value of MDM2 as a drug target for breast cancer therapy. For example, a chalcone derivative of this invention that inhibits MDM2 expression or binds to and disrupts the MDM2 protein complex may be a useful compound for the treatment of breast cancer. While not wishing to be bound by any theory, it is believed that the boronic acid analog might form a stronger salt bridge with K51 of MDM2 than the corresponding carboxylic acid analogs of chalcones and will selectively inhibit growth of breast cancer cells. Accordingly, a set of boronic acid-chalcone derivatives were designed and tested their ability to selectively kill breast cancer over normal breast epithelial cells.

In general, one embodiment of the invention relates to boronic-chalcone compounds of the general Formula I:

In one aspect, the present invention provides anti-cancer compounds having the formula:

(I)

In Formula (I), $X^1$ is —C= or —N=. $L^1$ is a bond, substituted or unsubstituted alkylene, or substituted or unsubstituted heteroalkylene.

$R^1$ has the formula:

(1)

(2)

(3)

The symbol n represents an integer from 0 to 1. Thus, where n is 0, the cyclic moiety of (2) is a 5-membered ring and where n is 1 the cyclic moiety of (2) is a 6-membered ring. $X^2$ is —N($R^4$)— or —CH($R^4$)—.

$L^2$, $L^3$, $L^4$, and $L^5$ are independently a bond, substituted or unsubstituted alkylene, substituted or unsubstituted heteroalkylene, or substituted or unsubstituted heterocycloalkylene.

$R^2$, $R^3$, and $R^4$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In some embodiments, where X is —C=, $L^2$ is a bond, $L^3$ is unsubstituted alkylene, $R^1$ is (1), and $R^1$ is para to —$L^1$—$B(OH)_2$, then $R^2$ is not substituted or unsubstituted aryl or substituted or unsubstituted heteroaryl. In other embodiments, where $L^2$ is a bond, $L^3$ is unsubstituted alkylene, and $R^1$ is (1), then $R^2$ is not substituted or unsubstituted aryl or substituted or unsubstituted heteroaryl.

$L^1$ may be a bond, substituted or unsubstituted $C_1$-$C_{20}$ alkylene, or substituted or unsubstituted 2 to 20 membered heteroalkylene. In some embodiments, $L^1$ is a bond, unsubstituted $C_1$-$C_{10}$ alkylene, or unsubstituted 2 to 10 membered heteroalkylene. $L^1$ may also be a bond, substituted or unsubstituted $C_1$-$C_{10}$ alkylene, or substituted or unsubstituted 2 to 10 membered heteroalkylene.

$L^2$, $L^3$, $L^4$, and $L^5$ may independently be a bond, substituted or unsubstituted $C_1$-$C_{20}$ alkylene, substituted or unsubstituted 2 to 20 membered heteroalkylene, or substituted or unsubstituted 3 to 8 membered heterocycloalkylene. $L^2$, $L^3$, $L^4$ and $L^5$ may also independently be a bond, unsubstituted $C_1$-$C_{10}$ alkylene, unsubstituted 2 to 10 membered heteroalkylene, or unsubstituted 3 to 8 membered heterocycloalkylene. In some embodiments, $L^2$, $L^3$, $L^4$, and $L^5$ are independently a bond, substituted or unsubstituted $C_1$-$C_{10}$ alkylene, substituted or unsubstituted 2 to 10 membered heteroalkylene, or substituted or unsubstituted 3 to 8 membered heterocycloalkylene.

$R^2$, $R^3$, and $R^4$ may independently be hydrogen, substituted or unsubstituted $C_1$-$C_{20}$ alkyl, substituted or unsubstituted 2 to 20 membered heteroalkyl, substituted or unsubstituted $C_3$-$C_8$ cycloalkyl, substituted or unsubstituted 3 to 8 membered heterocycloalkyl, substituted or unsubstituted aryl, or substituted or unsubstituted heteroaryl. In certain embodiments, $R^2$, $R^3$, and $R^4$ are independently hydrogen, substituted or unsubstituted $C_1$-$C_{10}$ alkyl, substituted or unsubstituted 2 to 10 membered heteroalkyl, substituted or unsubstituted $C_3$-$C_8$ cycloalkyl, substituted or unsubstituted 3 to 8 membered heterocycloalkyl, substituted or unsubstituted aryl, or substituted or unsubstituted heteroaryl.

In certain embodiments, $L^2$ is a bond, unsubstituted $C_1$-$C_{10}$ alkylene, unsubstituted 2 to 10 membered heteroalkylene, or unsubstituted 3 to 8 membered heterocycloalkylene. In another embodiment, $L^2$ is a bond, or unsubstituted 3 to 8 membered heterocycloalkylene. $L^2$ may also be a bond or piperazinylene.

$L^3$ may be a bond, unsubstituted $C_1$-$C_{10}$ alkylene, unsubstituted 2 to 10 membered heteroalkylene, or unsubstituted 3 to 8 membered heterocycloalkylene. In some embodiments, $L^3$ is unsubstituted $C_1$-$C_{10}$ alkylene. $L^3$ may also be unsubstituted $C_1$-$C_3$ alkenylene.

$R^2$ may be $R^{21}$-substituted or unsubstituted $C_1$-$C_{15}$ alkyl, $R^{21}$-substituted or unsubstituted 2 to 10 membered heteroalkyl, $R^{21}$-substituted or unsubstituted $C_3$-$C_8$ cycloalkyl, $R^{21}$-substituted or unsubstituted 3 to 8 membered heterocycloalkyl, $R^{21}$-substituted or unsubstituted aryl, or $R^{21}$-substituted or unsubstituted heteroaryl. $R^{21}$ is a halogen, —OH, —SH, —NH$_2$, —CF$_3$, —B(OH)$_2$, —C(O)NHOH, unsubstituted $C_1$-$C_{10}$ alkyl, unsubstituted 2 to 10 membered heteroalkyl, unsubstituted $C_3$-$C_8$ cycloalkyl, unsubstituted 3 to 8 membered heterocycloalkyl, unsubstituted aryl, unsubstituted heteroaryl, or —OR$^{22}$. $R^{22}$ is unsubstituted $C_1$-$C_{10}$ alkyl, unsubstituted 2 to 10 membered heteroalkyl, unsubstituted $C_3$-$C_8$ cycloalkyl, unsubstituted 3 to 8 membered heterocycloalkyl, unsubstituted aryl, unsubstituted heteroaryl, or —(CH$_2$)$_q$B(OH)$_2$, wherein q is an integer from 1 to 5. In some embodiments, q is 0 or 1.

In certain embodiments, $R^2$ is $R^{21}$-substituted or unsubstituted $C_1$-$C_{15}$ alkyl, or $R^{21}$-substituted or unsubstituted aryl. $R^2$ may also be unsubstituted $C_1$-$C_{15}$ alkyl, or $R^{21}$-substituted or unsubstituted aryl.

$R^{21}$ may be halogen, —OH, —SH, —NH$_2$, —CF$_3$, —B(OH)$_2$, —C(O)NHOH, unsubstituted $C_1$-$C_{10}$ alkyl, unsubstituted 2 to 10 membered heteroalkyl, unsubstituted $C_3$-$C_8$ cycloalkyl, unsubstituted 3 to 8 membered heterocycloalkyl, unsubstituted aryl, unsubstituted heteroaryl, or —OR$^{22}$. In some embodiments, $R^{21}$ is halogen, —C(O)NHOH, unsubstituted $C_1$-$C_{10}$ alkyl, unsubstituted 2 to 10 membered heteroalkyl, or —OR$^{22}$.

$R^{22}$ may be unsubstituted $C_1$-$C_{10}$ alkyl, or unsubstituted 2 to 10 membered heteroalkyl. $R^{22}$ may also be unsubstituted $C_1$-$C_{10}$ alkyl, or unsubstituted 2 to 10 membered heteroalkyl.

$L^4$ and $L^5$ may independently be a bond, unsubstituted $C_1$-$C_{10}$ alkylene, unsubstituted 2 to 10 membered heteroalkylene, or unsubstituted 3 to 8 membered heterocycloalkylene. $L^4$ and $L^5$ may also be unsubstituted $C_1$-$C_{10}$ alkylene. Alternatively, $L^4$ and $L^5$ are unsubstituted $C_1$-$C_3$ alkenylene.

$R^4$ may be unsubstituted $C_1$-$C_{10}$ alkyl, unsubstituted 2 to 10 membered heteroalkyl, unsubstituted $C_3$-$C_8$ cycloalkyl, unsubstituted 3 to 8 membered heterocycloalkyl, unsubstituted aryl, or unsubstituted heteroaryl. $R^4$ may also be unsubstituted $C_1$-$C_{10}$ alkyl.

In certain embodiments, $R^3$ is $R^{31}$-substituted or unsubstituted $C_1$-$C_{10}$ alkyl, $R^{31}$-substituted or unsubstituted 2 to 10 membered heteroalkyl, $R^{31}$-substituted or unsubstituted $C_3$-$C_8$ cycloalkyl, $R^{31}$-substituted or unsubstituted 3 to 8 membered heterocycloalkyl, $R^{31}$-substituted or unsubstituted aryl, or $R^{31}$-substituted or unsubstituted heteroaryl. $R^{31}$ is halogen, —OH, —SH, —NH$_2$, —CF$_3$, —B(OH)$_2$, —C(O)NHOH, unsubstituted $C_1$-$C_{10}$ alkyl, unsubstituted 2 to 10 membered heteroalkyl, unsubstituted $C_3$-$C_8$ cycloalkyl, unsubstituted 3 to 8 membered heterocycloalkyl, unsubstituted aryl, unsubstituted heteroaryl, or —OR$^{32}$. $R^{32}$ is unsubstituted $C_1$-$C_{10}$ alkyl, unsubstituted 2 to 10 membered heteroalkyl, unsubstituted $C_3$-$C_8$ cycloalkyl, unsubstituted 3 to 8 membered heterocycloalkyl, unsubstituted aryl, unsubstituted heteroaryl, or —(CH$_2$)$_m$B(OH)$_2$, wherein m is an integer from 1 to 5. In some embodiments, m is 0 or 1.

hi some embodiments, $R^3$ is $R^{31}$-substituted aryl. $R^{31}$ may be a halogen, —C(O)NHOH, unsubstituted $C_1$-$C_{10}$ alkyl, unsubstituted 2 to 10 membered heteroalkyl, or —OR$^{32}$. $R^{32}$ may be an unsubstituted $C_1$-$C_{10}$ alkyl, unsubstituted 2 to 10 membered heteroalkyl, or —(CH$_2$)$_m$B(OH)$_2$, wherein m is 1 to 5.

In certain embodiments, $R^1$ is para to —$L^1$—B(OH)$_2$. In other embodiments X is —C≡. In another embodiment, $L^1$ is a bond or methylene.

The invention further relates to a method for treating proliferative diseases such as cancers. More specifically, one embodiment of this invention provides a method of treating or preventing a tumor or cancer in a patient comprising administering to said patient in need thereof an effective amount of a compound having the Formula I-IX or a pharmaceutically-acceptable salt or in vivo cleavable prodrug thereof. Other aspects of the invention include methods for treating cancers mediated by MDM2. Examples of cancers that may be treated of prevented by the compounds of this invention include, but are not limited to, breast, colorectal, cervical, ovarian, brain, acute leukemia, gastric, non-small cell lung, pancreatic, and renal cancer.

The invention also features methods of combination therapy, such as a method for treating cancer, wherein the above methods further include providing radiation therapy or chemotherapy. The chemotherapy or radiation therapy may be administered before, concurrently, or after the administration of a disclosed compound according to the needs of the patient.

In a further aspect the present invention provides methods of inhibiting MDM2 expression in a mammal, comprising administering an amount of a compound effective to inhibit said expression, said compound having the Formula I-IX or a pharmaceutically acceptable salt or in vivo cleavable prodrug thereof.

The invention also relates to pharmaceutical compositions comprising an effective amount of an agent selected from compounds of Formulas I-IX or a pharmaceutically acceptable prodrug, pharmaceutically active metabolite, or pharmaceutically acceptable salt thereof.

Additional advantages and novel features of this invention shall be set forth in part in the description that follows, and in part will become apparent to those skilled in the art upon examination of the following specification or maybe learned by the practice of the invention. The advantages of the invention may be realized and attained by means of the instrumentalities, combinations, compositions, and methods particularly pointed out in the appended claims.

BRIEF DESCRIPTION OF THE DRAWINGS

The accompanying drawings, which are incorporated herein and form a part of the specification, illustrate non-limiting embodiments of the present invention, and together with the description, serve to explain the principles of the invention.
In the Figures:
FIG. 4(a, b, and c) graphically demonstrates a 96 hour MTT assay using compound 2 at various times.

DETAILED DESCRIPTION OF THE INVENTION

The invention features novel boronic chalcone compounds having Formulas I-IX, pharmaceutical compositions thereof, and methods of using such compounds and compositions. The inventive compounds of the Formulas I-IX are useful, for example, for treating a tumor or cancer in a patient. Such compounds have particular utility as therapeutic agents for diseases that can be treated by the inhibition of MDM2 expression.

Abbreviations used herein have their conventional meaning within the chemical and biological arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e. unbranched) or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds (e.g. alkenyl) or triple bonds (e.g. alkynyl). Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups which are limited to hydrocarbon groups are termed "homoalkyl".

The term "alkylene" by itself or as part of another substituent means a divalent radical derived from an alkyl, as exemplified, but not limited, by —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. An "alkenylene" is a divalent radical derived from an alkenyl, as exemplified, but not limited, by —$CH_2$=$CH_2CH_2$—.

The term "heteroalkyl," by itself or in combination with another term, means, unless otherwise stated, a stable straight or branched chain, or cyclic hydrocarbon radical, or combinations thereof, consisting of at least one carbon atoms and at least one heteroatom selected from the group consisting of O, N, P, Si and S, and wherein the nitrogen and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, O—$CH_3$, —O—$CH_2$—$CH_3$, and —CN. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)2R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

An "alkylesteryl," as used herein, refers to a moiety having the formula R'—C(O)O—R", wherein R' is an alkylene moiety and R" is an alkyl moiety.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent derivatives of aryl and heteroaryl, respectively.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). However, the term "haloaryl," as used herein is menat to cover only aryls substituted with one or more halogens.

The term "oxo" as used herein means an oxygen that is double bonded to a carbon atom.

Each of above terms (e.g., "alkyl," "heteroalkyl," "cycloalkyl, and "heterocycloalkyl", "aryl," "heteroaryl" as well as their divalent radical derivatives) are meant to include both substituted and unsubstituted forms of the indicated radical. Preferred substituents for each type of radical are provided below.

Substituents for alkyl, heteroalkyl, cycloalkyl, heterocycloalkyl monovalent and divalent derivative radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR, =N—OR', —NR'R", —SR', -halogen, —SiR'R"R"', —OC(O)R', —C(O)R', —$CO_2$R', —CONR'R", —OC(O)NR'R", —NR"C(O)R', —NR'—C(O) NR"R"', —NR"C(O)$_2$R', —NR—C(NR'R"R"')=NR"", —NR—C(NR'R")=NR"', —S(O)R, —S(O)$_2$R', —S(O)$_2$NR'R", —NRSO$_2$R', —CN and —NO$_2$ in a number ranging from zero to (2m'+1), where m' is the total number of carbon atoms in such radical. R', R", R"' and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. When a compound of the invention includes more than one R group, for example, each of the R groups is independently selected as are each R', R", R"' and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From above discussion of substituents, one of skill in art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for alkyl radicals above, exemplary substituents for aryl and heteroaryl groups (as well as their divalent derivatives) are varied and are selected from, for example: halogen, —OR', —NR'R", —SR', -halogen, —SiR'R"R"', —OC—O—R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN and —NO$_2$, —R', —N$_3$, —CH(Ph)$_2$, fluoro($C_1$-$C_4$)alkoxy, and fluoro($C_1$-$C_4$)alkyl, in a number ranging from zero to the total number of open valences on aromatic ring system; and where R', R", R"' and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the invention includes more than one R group, for example, each of the R groups is independently selected as are each R', R", R"' and R"" groups when more than one of these groups is present.

Two of the substituents on adjacent atoms of aryl or heteroaryl ring may optionally form a ring of the formula —T—C(O)—(CRR')$_q$—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula —A—(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of aryl or heteroaryl ring may optionally be replaced with a substituent of the formula —(CRR')s-X'—(C"R"')$_d$—, where s and d are independently integers of from 0 to 3, and X' is —O—, —NR'—, —S—, —S(O)—, —S(O)$_2$—, or —S(O)$_2$NR'—. The substituents R, R', R" and R"' are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "heteroatom" or "ring heteroatom" is meant to include oxygen (O), nitrogen (N), sulfur (S), phosphorus (P), and silicon (Si).

The compounds of the present invention may exist as salts. The present invention includes such salts. Examples of applicable salt forms include hydrochlorides, hydrobromides, sulfates, methanesulfonates, nitrates, maleates, acetates, citrates, fumarates, tartrates (eg (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

The compounds of the present invention may also contain unnatural proportions of atomic isotopes at one or more of atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are encompassed within the scope of the present invention.

The term "pharmaceutically acceptable salts" is meant to include salts of active compounds which are prepared with relatively nontoxic acids or bases, depending on the particular substituent moieties found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al, "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

Certain of the compounds of this invention, in pharmaceutical dosage form, may be used as a method of treating a cancer or as a prophylactic agent for preventing a disease or condition from manifesting itself. Accordingly, this invention further includes compositions including, but not limited to, solvates, pharmaceutically acceptable prodrugs, pharmaceutically active metabolites, and pharmaceutically acceptable salts of compounds of Formulas I-IX. The term "solvate" refers to an aggregate of a molecule with one or more solvent molecules.

In certain pharmaceutical dosage forms, the pro-drug form of the compounds according to the present invention may be preferred. A "prodrug" is a compound that may be converted under physiological conditions or by solvolysis to the specified compound or to a pharmaceutically acceptable salt of such compound.

A "pharmaceutically active metabolite" is a pharmacologically active product produced through metabolism in the body of a specified compound or salt thereof. Metabolites of a compound may be identified using routine techniques known in the art and their activities determined using tests such as those described herein.

Prodrugs and active metabolites of a compound may be identified using routine techniques known in the art. Various forms of prodrugs are known in the art. For examples of such prodrug derivatives, see, for example, a) *Design of Prodrugs,* edited by H. Bundgaard, (Elsevier, 1985) and *Methods in Enzymology,* Vol. 42, p. 309-396, edited by K. Widder, et al. (Academic Press, 1985); b) *A Textbook of Drug Design and Development,* edited by Krogsgaard-Larsen and H. Bundgaard, Chapter 5 "Design and Application of Prodrug" (H. Bundgaard p. 113-191 (1991)); c) H. Bundgaard, *Advanced Drug Delivery Reviews,* 8, 1-38 (1992); d) H. Bundgaard, et al., *Journal of Pharmaceutical Sciences,* 77:285 (1988); and e) N. Kakeya, et al., *Chem. Pharm. Bull.,* 32: 692 (1984).

The compounds of this invention, including prodrug forms of these agents, can be provided in the form of pharmaceutically acceptable salts. As used herein, the term pharmaceutically acceptable salts or complexes refers to appropriate salts or complexes of the active compounds according to the present invention which retain the desired biological activity of the parent compound and exhibit limited toxicological effects to normal cells. Nonlimiting examples of such salts are acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, and polyglutamic acid, among others.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

The terms "a," "an," or "a(n)", when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

Anti-Cancer Compounds

In one aspect, the present invention provides anti-cancer compounds having the formula:

(I)

In Formula (I), $X^1$ is —C= or —N=. $L^1$ is a bond, substituted or unsubstituted alkylene, or substituted or unsubstituted heteroalkylene.

$R^1$ has the formula:

(1)

(2)

(3)

The symbol n represents an integer from 0 to 1. Thus, where n is 0, the cyclic moiety of (2) is a 5-membered ring and where n is 1 the cyclic moiety of (2) is a 6-membered ring. $X^2$ is —N($R^4$)— or —CH($R^4$)—.

$L^2$, $L^3$, $L^4$, and $L^5$ are independently a bond, substituted or unsubstituted alkylene, substituted or unsubstituted heteroalkylene, or substituted or unsubstituted heterocycloalkylene.

$R^2$, $R^3$, and $R^4$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In some embodiments, where X is —C=, $L^2$ is a bond, $L^3$ is unsubstituted alkylene, $R^1$ is (1), and $R^1$ is para to —$L^1$—B(OH)$_2$, then $R^2$ is not substituted or unsubstituted aryl or substituted or unsubstituted heteroaryl. In other embodiments, where $L^2$ is a bond, $L^3$ is unsubstituted alkylene, and $R^1$ is (1), then $R^2$ is not substituted or unsubstituted aryl or substituted or unsubstituted heteroaryl.

$L^1$ may be a bond, substituted or unsubstituted $C_1$-$C_{20}$ alkylene, or substituted or unsubstituted 2 to 20 membered heteroalkylene. In some embodiments, $L^1$ is a bond, unsubstituted $C_1$-$C_{10}$ alkylene, or unsubstituted 2 to 10 membered heteroalkylene. $L^1$ may also be a bond, substituted or unsubstituted $C_1$-$C_{10}$ alkylene, or substituted or unsubstituted 2 to 10 membered heteroalkylene.

$L^2$, $L^3$, $L^4$, and $L^5$ may independently be a bond, substituted or unsubstituted $C_1$-$C_{20}$ alkylene, substituted or unsubstituted 2 to 20 membered heteroalkylene, or substituted or unsubstituted 3 to 8 membered heterocycloalkylene. $L^2$, $L^3$, $L^4$ and $L^5$ may also independently be a bond, unsubstituted $C_1$-$C_{10}$ alkylene, unsubstituted 2 to 10 membered heteroalkylene, or unsubstituted 3 to 8 membered heterocycloalkylene. In some embodiments, $L^2$, $L^3$, $L^4$, and $L^5$ are independently a bond, substituted or unsubstituted $C_1$-$C_{10}$ alkylene, substituted or unsubstituted 2 to 10 membered heteroalkylene, or substituted or unsubstituted 3 to 8 membered heterocycloalkylene.

$R^2$, $R^3$, and $R^4$ may independently be hydrogen, substituted or unsubstituted $C_1$-$C_{20}$ alkyl, substituted or unsubstituted 2 to 20 membered heteroalkyl, substituted or unsubstituted $C_3$-$C_8$ cycloalkyl, substituted or unsubstituted 3 to 8 membered heterocycloalkyl, substituted or unsubstituted aryl, or substituted or unsubstituted heteroaryl. In certain embodiments, $R^2$, $R^3$, and $R^4$ are independently hydrogen, substituted or unsubstituted $C_1$-$C_{10}$ alkyl, substituted or unsubstituted 2 to 10 membered heteroalkyl, substituted or unsubstituted $C_3$-$C_8$ cycloalkyl, substituted or unsubstituted 3 to 8 membered heterocycloalkyl, substituted or unsubstituted aryl, or substituted or unsubstituted heteroaryl.

In certain embodiments, $L^2$ is a bond, unsubstituted $C_1$-$C_{10}$ alkylene, unsubstituted 2 to 10 membered heteroalkylene, or unsubstituted 3 to 8 membered heterocycloalkylene. In another embodiment, $L^2$ is a bond, or unsubstituted 3 to 8 membered heterocycloalkylene. $L^2$ may also be a bond or piperazinylene.

L³ may be a bond, unsubstituted $C_1$-$C_{10}$ alkylene, unsubstituted 2 to 10 membered heteroalkylene, or unsubstituted 3 to 8 membered heterocycloalkylene. In some embodiments, L³ is unsubstituted $C_1$-$C_{10}$ alkylene. L³ may also be unsubstituted $C_1$-$C_3$ alkenylene.

R² may be $R^{21}$-substituted or unsubstituted $C_1$-$C_{15}$ alkyl, $R^{21}$-substituted or unsubstituted 2 to 10 membered heteroalkyl, $R^{21}$-substituted or unsubstituted $C_3$-$C_8$ cycloalkyl, $R^{21}$-substituted or unsubstituted 3 to 8 membered heterocycloalkyl, $R^{21}$-substituted or unsubstituted aryl, or $R^{21}$-substituted or unsubstituted heteroaryl. $R^{21}$ is a halogen, —OH, —SH, —$NH_2$, —$CF_3$, —$B(OH)_2$, —C(O)NHOH, unsubstituted $C_1$-$C_{10}$ alkyl, unsubstituted 2 to 10 membered heteroalkyl, unsubstituted $C_3$-$C_8$ cycloalkyl, unsubstituted 3 to 8 membered heterocycloalkyl, unsubstituted aryl, unsubstituted heteroaryl, or —$OR^{22}$. $R^{22}$ is unsubstituted $C_1$-$C_{10}$ alkyl, unsubstituted 2 to 10 membered heteroalkyl, unsubstituted $C_3$-$C_8$ cycloalkyl, unsubstituted 3 to 8 membered heterocycloalkyl, unsubstituted aryl, unsubstituted heteroaryl, or —$(CH_2)_qB(OH)_2$, wherein q is an integer from 1 to 5. In some embodiments, q is 0 or 1.

In certain embodiments, R² is $R^{21}$-substituted or unsubstituted $C_1$-$C_{15}$ alkyl, or $R^{21}$-substituted or unsubstituted aryl. R² may also be unsubstituted $C_1$-$C_{15}$ alkyl, or $R^{21}$-substituted or unsubstituted aryl.

$R^{21}$ may be halogen, —OH, —SH, —$NH_2$, —$CF_3$, —$B(OH)_2$, —C(O)NHOH, unsubstituted $C_1$-$C_{10}$ alkyl, unsubstituted 2 to 10 membered heteroalkyl, unsubstituted $C_3$-$C_8$ cycloalkyl, unsubstituted 3 to 8 membered heterocycloalkyl, unsubstituted aryl, unsubstituted heteroaryl, or —$OR^{22}$. In some embodiments, $R^{21}$ is halogen, —C(O)NHOH, unsubstituted $C_1$-$C_{10}$ alkyl, unsubstituted 2 to 10 membered heteroalkyl, or —$OR^{22}$.

$R^{22}$ may be unsubstituted $C_1$-$C_{10}$ alkyl, or unsubstituted 2 to 10 membered heteroalkyl. $R^{22}$ may also be unsubstituted $C_1$-$C_{10}$ alkyl, or unsubstituted 2 to 10 membered heteroalkyl.

L⁴ and L⁵ may independently be a bond, unsubstituted $C_1$-$C_{10}$ alkylene, unsubstituted 2 to 10 membered heteroalkylene, or unsubstituted 3 to 8 membered heterocycloalkylene. L⁴ and L⁵ may also be unsubstituted $C_1$-$C_{10}$ alkylene. Alternatively, L⁴ and L⁵ are unsubstituted $C_1$-$C_3$ alkenylene.

R⁴ may be unsubstituted $C_1$-$C_{10}$ alkyl, unsubstituted 2 to 10 membered heteroalkyl, unsubstituted $C_3$-$C_8$ cycloalkyl, unsubstituted 3 to 8 membered heterocycloalkyl, unsubstituted aryl, or unsubstituted heteroaryl. R⁴ may also be unsubstituted $C_1$-$C_{10}$ alkyl.

In certain embodiments, R³ is $R^{31}$-substituted or unsubstituted $C_1$-$C_{10}$ alkyl, $R^{31}$-substituted or unsubstituted 2 to 10 membered heteroalkyl, $R^{31}$-substituted or unsubstituted $C_3$-$C_8$ cycloalkyl, $R^{31}$-substituted or unsubstituted 3 to 8 membered heterocycloalkyl, $R^{31}$-substituted or unsubstituted aryl, or $R^{31}$-substituted or unsubstituted heteroaryl. $R^{31}$ is halogen, —OH, —SH, —$NH_2$, —$CF_3$, —$B(OH)_2$, —C(O)NHOH, unsubstituted $C_1$-$C_{10}$ alkyl, unsubstituted 2 to 10 membered heteroalkyl, unsubstituted $C_3$-$C_8$ cycloalkyl, unsubstituted 3 to 8 membered heterocycloalkyl, unsubstituted aryl, unsubstituted heteroaryl, or —$OR^{32}$. $R^{32}$ is unsubstituted $C_1$-$C_{10}$ alkyl, unsubstituted 2 to 10 membered heteroalkyl, unsubstituted $C_3$-$C_8$ cycloalkyl, unsubstituted 3 to 8 membered heterocycloalkyl, unsubstituted aryl, unsubstituted heteroaryl, or —$(CH_2)_mB(OH)_2$, wherein m is an integer from 1 to 5. In some embodiments, m is 0 or 1.

In some embodiments, R³ is $R^{31}$-substituted aryl. $R^{31}$ may be a halogen, —C(O)NHOH, unsubstituted $C_1$-$C_{10}$ alkyl, unsubstituted 2 to 10 membered heteroalkyl, or —$OR^{32}$. $R^{32}$ may be an unsubstituted $C_1$-$C_{10}$ alkyl, unsubstituted 2 to 10 membered heteroalkyl, or —$(CH_2)_mB(OH)_2$, wherein m is 1 to 5.

In certain embodiments, R¹ is para to —L¹—$B(OH)_2$. In other embodiments X is —C═. In another embodiment, L¹ is a bond or methylene.

The inventive compounds may be prepared using the reaction routes and synthesis schemes as described below, employing the techniques available in the art using starting materials that are readily available. For example, in one embodiment boronic chalcone compounds, which is based upon a chemical structure I:

can be prepared according to the reaction schemes shown below in the Examples.

It is important to note that the methods of synthesizing the disclosed compounds are general examples, and one of ordinary skill may readily determine or provide alternative syntheses for producing compounds according to the present invention without engaging in undue experimentation. Using the general and specific synthetic methodologies described herein, a number of the chemical compounds as set forth in FIG. 1 were synthesized.

The compounds of the present invention are useful for treating or preventing benign and malignant tumors, including various cancers such as, cervical, anal and oral cancers, stomach, colon, bladder, rectal, liver, pancreatic, lung, breast, cervix uteri, corpus uteri, ovary, prostate, testis, renal, brain/cns (e.g., gliomas), head and neck, eye or ocular, throat, skin melanoma, acute lymphocytic leukemia, acute myelogenous leukemia, Ewing's Sarcoma, Kaposi's Sarcoma, basal cell carcinoma and squamous cell carcinoma, small cell lung cancer, mouth/pharynx, esophageal, larynx, kidney and lymphoma, among others. In addition, conditions such as neurofibromatosis, tuberous sclerosis (each of which conditions produces benign tumors of the skin), hemangiomas and lymphangiogenesis, among others, may be treated effectively with compounds according to the present invention.

Methods of treating tumors and/or cancer according to the present invention comprise administering to a patient in need thereof an effective amount of one or more compounds according to the present invention or a pharmaceutically acceptable salt or in vivo cleavable prodrug thereof.

The invention also features methods of combination therapy, such as a method for treating cancer, wherein the above methods further include providing radiation therapy or chemotherapy, for example, with mitotic inhibitors such as a taxane or a vinca alkaloid. Examples of mitotic inhibitors include paclitaxel, docetaxel, vincristine, vinblastine, vinorelbine, and vinflunine. Other therapeutic combinations include a MEK inhibitor of the invention and an anticancer agent such as cisplatin, 5-fluorouracil or 5-fluoro-2-4(1H, 3H)-pyrimidinedione (5FU), flutamide, and gemcitabine. The chemotherapy or radiation therapy may be administered before, concurrently, or after the administration of a disclosed compound according to the needs of the patient.

Numerous biological assays have been used and are accepted by those skilled in the art to assess the anti-tumor and anti-cancer activity of compounds according to the present invention. Any of these methods can be used to evaluate the activity of the compounds disclosed herein. One common method of assessing activity is through the use of test panels of cancer cell lines. These tests evaluate the in vitro anti-cancer activity of particular compounds in cancer cell lines, and provide predictive data with respect to the use of tested compounds in vivo. Other assays include in vivo evaluations of the compound's effect on human or in an appropriate animal model, for example, using mouse tumor cells implanted into or grafted onto mice or in other appropriate animal models.

In the case of testing the anti-cancer activity of compounds according to the present invention, an assay based on human breast cancer MDA-MB-231 (estrogen receptor negative) and wtMCF7 (estrogen receptor positive) cells may be employed as described in Example 6. In this assay, cells are seeded onto a 96-well plate and treated with a compound according to the present invention at a known concentration. The cell numbers are counted and compared against controls. Percent inhibition is readily determined from the data obtained. Other methods known in the art may also be used without undue experimentation to assay the anti-cancer activity of the disclosed compounds.

Therapeutically effective amounts of the compounds of the invention may also be used to treat diseases mediated by expression of MDM2. An "effective amount" is intended to mean that amount of compound that, when administered to a mammal in need of such treatment, is sufficient to inhibit or attenuate expression of MDM2. Thus, for example, a therapeutically effective amount of a compound selected from Formulas I-IX, or a salt, active metabolite or prodrug thereof, is a quantity sufficient to modulate, regulate, or inhibit expression of MDM2.

The amount of a given agent that will correspond to such an amount will vary depending upon factors such as the particular compound, disease condition and its severity, the identity (e.g., weight) of the mammal in need of treatment, but can nevertheless be routinely determined by one skilled in the art. "Treating" is intended to mean at least the mitigation of a disease condition in a mammal, such as a human, and includes, but is not limited to, preventing the disease condition from occurring in a mammal, particularly when the mammal is found to be predisposed to having the disease condition but has not yet been diagnosed as having it; modulating and/or inhibiting the disease condition; and/or alleviating the disease condition.

In order to use a compound of the Formula I-IX, or a pharmaceutically acceptable salt or in vivo cleavable prodrug thereof, for the therapeutic treatment (including prophylactic treatment) of mammals including humans, it is normally formulated in accordance with standard pharmaceutical practice as a pharmaceutical composition. According to this aspect of the invention there is provided a pharmaceutical composition that comprises a compound of the Formula I-IX, or a pharmaceutically acceptable salt or in vivo cleavable prodrug thereof, as defined hereinbefore in association with a pharmaceutically acceptable diluent or carrier.

The compounds of this invention may be incorporated into formulations for all routes of administration including for example, oral, topical and parenteral including intravenous, intramuscular, eye or ocular, intraperitoneal, intrabuccal, transdermal and in suppository form.

In the pharmaceutical aspect according to the present invention, the compound according to the present invention is formulated preferably in admixture with a pharmaceutically acceptable carrier, excipient or additive. In general, it is preferable to administer the pharmaceutical composition in orally administrable form, but for treatment of a number of conditions, a number of other formulations may be administered via a topical, parenteral, intravenous, intramuscular, transdermal, buccal, subcutaneous, suppository or other route, including an eye or ocular route. Intravenous and intramuscular formulations are preferably administered in sterile saline. Of course, one of ordinary skill in the art may modify the formulations within the teachings of the specification to provide numerous formulations for a particular route of administration without rendering the compositions of the present invention unstable or compromising their therapeutic activity. In particular, the modification of the present compounds to render them more soluble in water or other vehicle, for example, may be easily accomplished by minor modifications (salt formulation, esterification, etc.) which are well within the ordinary skill in the art. It is also well within the skill of those skilled in the art to modify the route of administration and dosage regimen of a particular compound in order to manage the pharmacokinetics of the present compounds for maximum beneficial effect to the patient.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, or intramuscular dosing or as a suppository for rectal dosing). For example, compositions intended for oral use may contain, for example, one or more coloring, sweetening, flavoring and/or preservative agents.

Suitable pharmaceutically-acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), coloring agents, flavoring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavoring and coloring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavoring and preservative agents.

Syrups and elixirs may be formulated with sweetening agents such as glycerol, propylene glycol, sorbitol, aspartame or sucrose, and may also contain a demulcent, preservative, flavoring and/or coloring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedures well known in the art.

Compositions for administration by insufflation may be in the form of a finely divided powder containing particles of average diameter of, for example, 30 µm or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurized aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulations, see Chapter 25.2 in Volume 5 of *Comprehensive Medicinal Chemistry* (Corwin Hansch; Chairman of Editorial Board), Pergamon Press 1990, which is specifically incorporated herein by reference.

The amount of a compound of this invention that is combined with one or more excipients to produce a single dosage form will necessarily vary depending upon the host treated and the particular route of administration. For example, a formulation intended for oral administration to humans will may contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on routes of administration and dosage regimes, see Chapter 25.3 in Volume 5 of *Comprehensive Medicinal Chemistry* (Corwin Hansen; Chairman of Editorial Board), Pergamon Press 1990, which is specifically incorporated herein by reference.

The size of the dose for therapeutic or prophylactic purposes of a compound of Formula I-IX will naturally vary according to the nature and severity of the conditions, the age and sex of the animal or patient and the route of administration, according to well known principles of medicine.

In one aspect of this invention, the compounds of this invention or pharmaceutical salts or prodrugs thereof may be formulated into pharmaceutical compositions for administration to animals or humans to treat or prevent solid tumors or cancer.

EXAMPLES

In order to illustrate the invention, the following examples are included. However, it is to be understood that these examples do not limit the invention and are only meant to suggest a method of practicing the invention. Persons skilled in the art will recognize that the chemical reactions described may be readily adapted to prepare a number of other boronic acid aryl analogs of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

In the examples below, unless otherwise indicated all temperatures are set forth in degrees Celsius. Reagents were purchased from commercial suppliers such as Aldrich Chemical Co., Lancaster, TCI or Maybridge, and used without further purification unless otherwise indicated. The reactions set forth below were done generally under a positive pressure of nitrogen or argon or with a drying tube (unless otherwise stated) in anhydrous solvents. The reaction flasks were typically fitted with rubber septa for the introduction of substrates and reagents via syringe. Glassware was oven dried and/or heat dried.

Example 1

Figure 1:
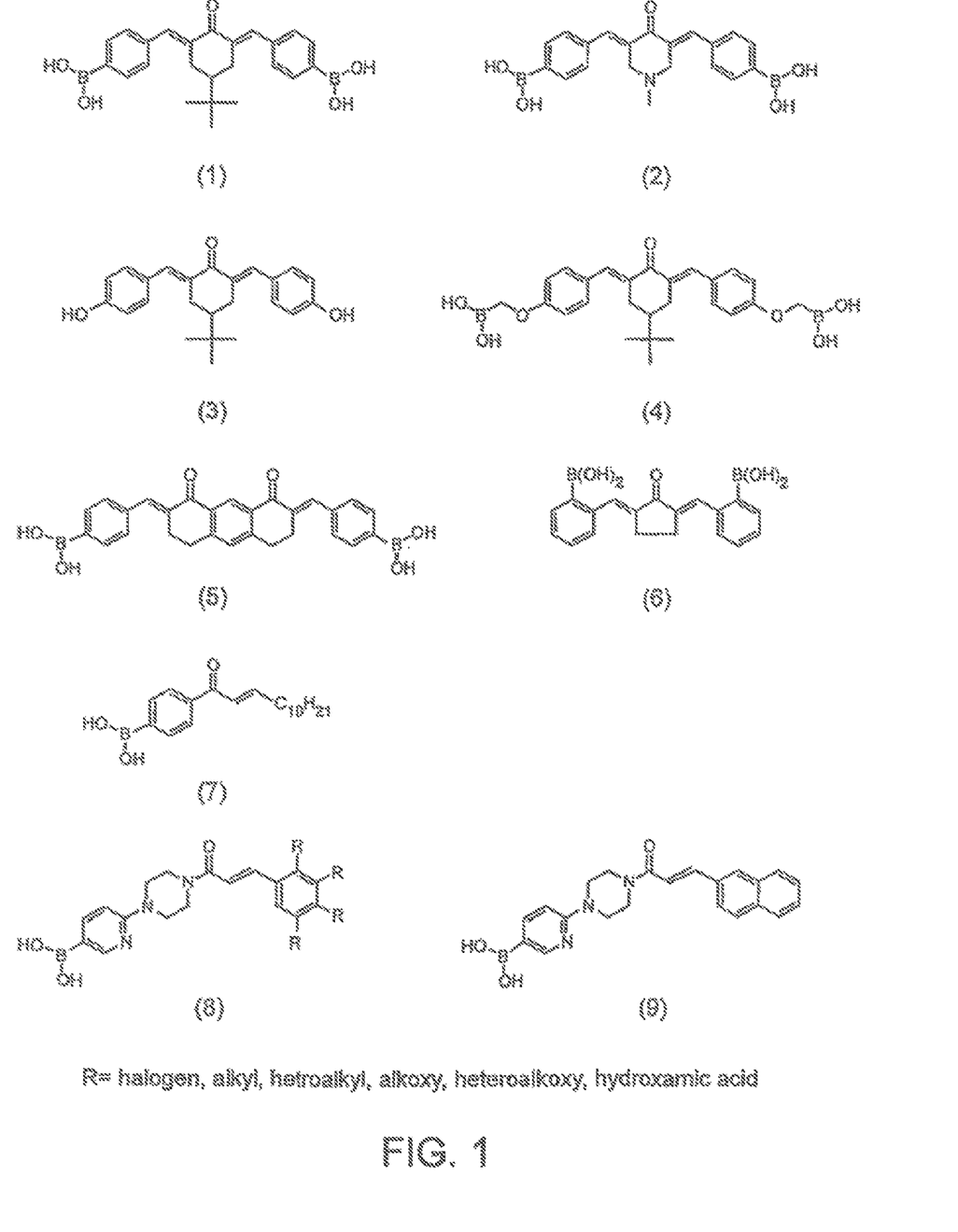
FIG. 1 schematically depicts the compounds of the present invention.

Schemes for Compounds 1, 2, and 6 as Shown in FIG. 1

X = N; R = H, Me, Et, t-Bu, allyl; R' = R'' = H, halogen, Me, OMe, OH, B(OH)$_2$ Example 2

Schemes for Compounds 3 and 4 as Shown in FIG. 1

(a) KOH, MeOH, reflux, (b) KH, Pinacol (Bromomethyl)boronate, Et$_2$O, 18-crown-6

Example 3

Schemes for Compound 5 as Shown in FIG. 1

Example 4

Schemes for Compound 7 as Shown in FIG. 1

Example 5

Schemes for Compounds 8 and 9 as Shown in FIG. 1

-continued

Example 6

Cytotoxicity of Boronic Acid Aryl Analogs

The cytotoxicity of the boronic acid aryl analogs ere evaluated and compared by MTT survival assays of human breast cancer MDA-MB-435, MDA-MB-231, Wt-MCF7, and MCF-10A cells treated at different concentrations of the analogs 1 and 2.

Cell Lines and Culture Conditions

Human breast cancer MDA-MB-231 (estrogen receptor negative) and MCF-7 (estrogen receptor positive) cells were maintained in DMEM medium (Mediatech, Herndon, Va.) supplemented with 5% fetal bovine serum (HyClone, Logan, Utah) and 2 mM L-analyl-L-glutamine (Mediatech). Normal breast epithelial cell lines, MCF-10A and MCF-12A, were maintained in 5% and 10% horse serum in 1:1 DMEM/F12 media, respectively, supplemented with 0.02 µg/mL EGF (Sigma, St. Louis, Mo.), 0.01 mg/mL insulin (Sigma), and 0.1 µg/mL cholera toxin (Sigma). Cells were incubated at 37° C., in 95% humidity, in a 5% $CO_2$ atmosphere.

MTT Assay

Figure 2:
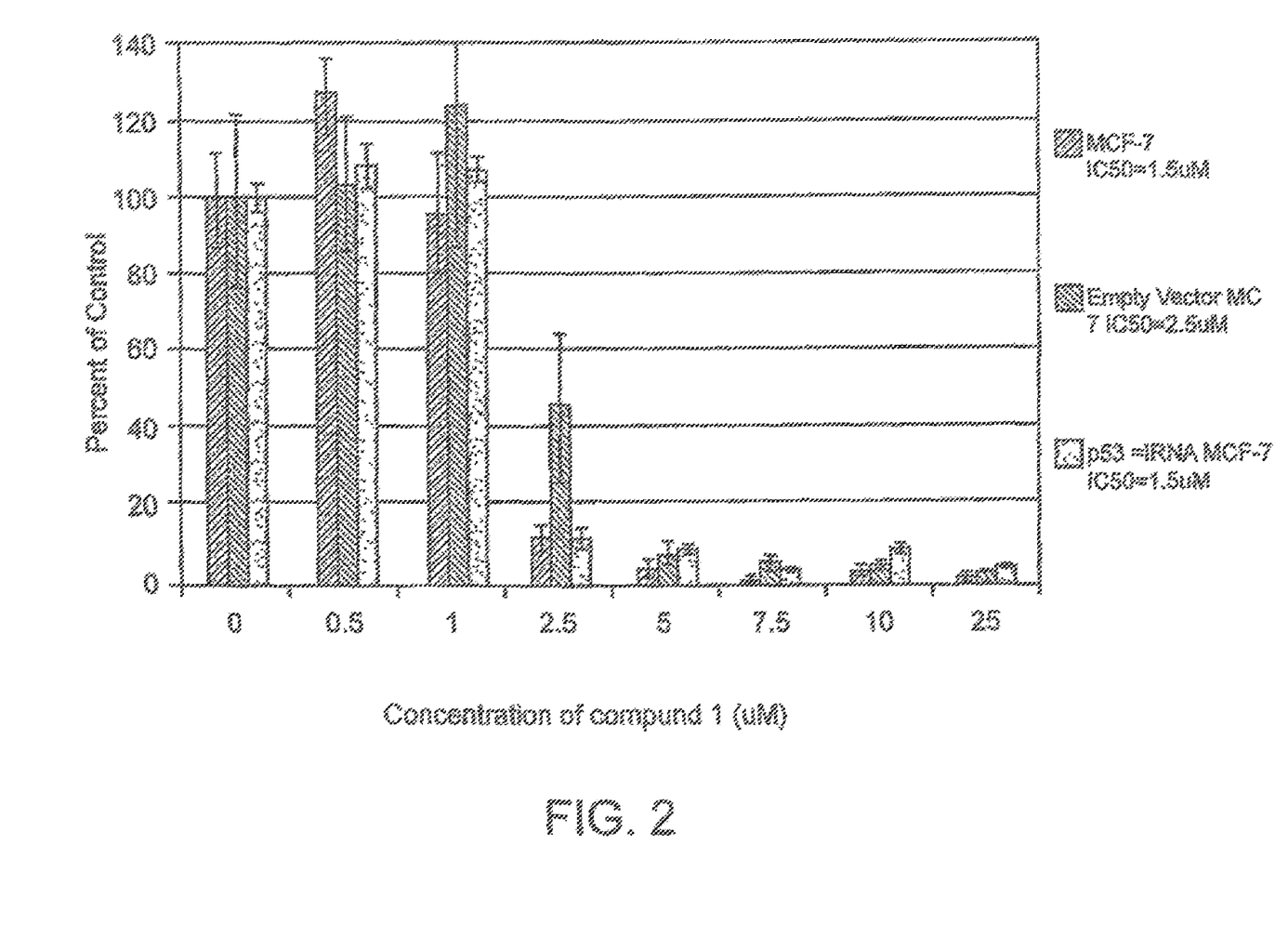
FIG. 2 graphically demonstrates a 96 hour MTT assay using compound 1.
Figure 4:
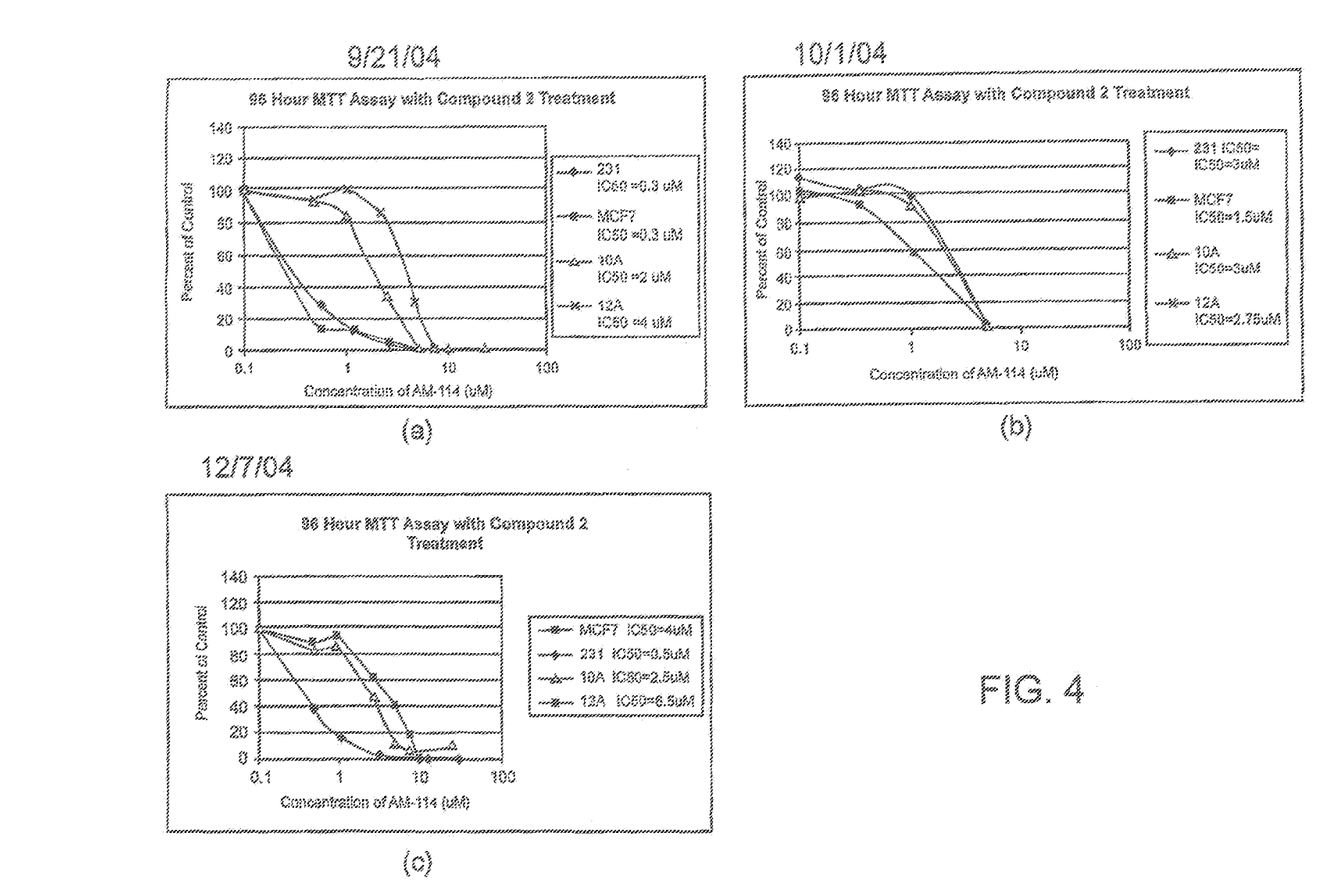

The MTT Colorimetric assay and cell counts were used to determine growth inhibition. Cells were plated at a cell density of 2500, 3000, 9000, and 13000 cells per well in 96-well plates for MCF-7, MDA-MB-231, MCF-10A, and MCF-12A cell lines, respectively. Cells were allowed to attach for 24 hours and the medium was changed. Chalcone derivatives were, dissolved in DMSO (Sigma) at 10 mM concentrations. Cells in quadruplicate were exposed to either the control concentration of 25 µM DMSO, or chalcone concentrations of 0.5-25 µM for 96 hours. After 96 hours the media was aspirated, 100 µL of 1 mg/mL MTT solution (Sigma) diluted in serum free media was added to each well and incubated for 4 hours. The MTT solution was removed, and the formazan crystals were dissolved in 200 µL of 1:1 (v/v) DMSO:ethanol for 20 minutes at ambient temperature. Absorbance was determined at A540 nm. $IC_{50}$ values were determined from log plots of percent of control vs concentration, see FIGS. 2 and 4. Each experiment was plated in quadruplicate and was performed three times.

Cell Growth Assay

Cells were plated at a cell density of 5,000 cells/well in 24-well plates. Cells were allowed to attach for 24 hours and the medium was changed. Cells in triplicate were exposed to either the control concentration of 10 µM DMSO, or 10 µM chalcone concentration for 24, 48, 72, and 96 hours. Every 24 hours, the cells the cells were detached by trypsinization and counted using a Coulter particle counter (Becton Dickinson, Franklin Lakes, N.J.).

Colony Formation

Cells were plated at a cell density of 500 cells/well in 6-well plates. Cells were allowed to attach for 24 hours and the medium was changed. Cells in triplicate were exposed to either the control concentration of 10 µM DMSO, 5 µM, or 10 µM chalcone concentration for 24, 48, 72, and 96 hours. On completion of the treatment period, the media was replaced with culture media appropriate to cell type. Media was changed every two days. 8 days after the completion of the treatment period, the media was removed and the cells were stained with 0.5% crystal violet in a 25% methanol and 75% water solution. Colonies of 50 or more cells were counted, and the average of triplicate wells was determined. Percentage of survival was determined by comparison of treated cells to control cells.

Figure 3:
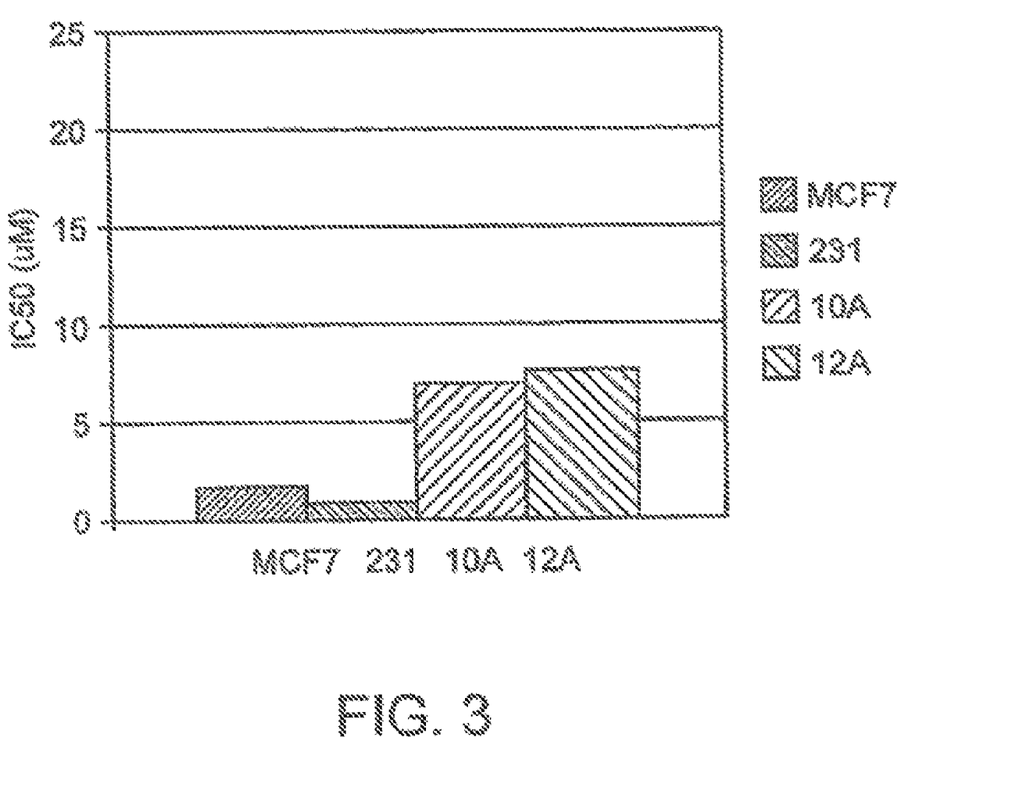
FIG. 3 graphically demonstrates $IC_{50}$ values of breast cancer and normal cell lines treated with compound 1 for 96 hours.

Results $IC_{50}$ values were used to determine growth inhibition in the presence of chalcone derivatives, see FIG. 3. In the presence of boronic chalcone 1, cell growth in the human breast cancer cell lines MDA-MB-231 and MCF-7 is inhibited, shown by the $IC_{50}$ of 1.0 µM. Cell growth in the normal breast epithelial cell lines MCF-10A and MCF-12A is less inhibited, shown by the higher $IC_{50}$ values ranging from 17-23 µM. The results from the MTT assays were validated by direct comparison to the cell growth assay.

$IC_{50}$ values were used to determine growth inhibition in the presence of chalcone derivatives. In the presence of boronic chalcone 2, cell growth in the human breast cancer cell lines MDA-MB-231 and MCF-7 is inhibited, shown by the $IC_{50}$ of 1.3 and 1.9 µM, respectively. Cell growth in the normal breast epithelial cell lines MCF-10A and MCF-12A is less inhibited, shown by the higher $IC_{50}$ values ranging from 2.5-4.4 µM, shown in Table 1. The results from the MTT assays were validated by direct comparison to the cell growth assay.

TABLE 1

Chalcones Inhibit Growth of Human Breast Cell Lines[a]
$IC_{50}$ Vaules Expressed in µM

| | MCF7 | MDA-MB-231 | MCF-10A | MCF-12A |
|---|---|---|---|---|
| Compound 2 | 1.9 | 1.3 | 2.5 | 4.4 |

[a]$IC_{50}$ values expressed in uM; see biology section for details of the MTT assay.

The foregoing description is considered as illustrative only of the principles of the invention. Further, since numerous modifications and changes will be readily apparent to those skilled in the art, it is not desired to limit the invention to the exact construction and process shown as described above. Accordingly, all suitable modifications and equivalents maybe resorted to falling within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

What is claimed is:

1. A method of treating breast cancer in a patient in need thereof comprising administering to the patient an effective amount of a compound of formula:

wherein
X¹ is C=;
L¹ is a bond;
R¹ is para to —L¹—B(OH)₂ and has formula:

(2)

n is 1;
X² is —N— or —CH—;
R³ is substituted aryl, wherein substituted aryl is and
R⁴ is substituted or unsubstituted alkyl.

2. The method of claim 1, wherein the compound having formula:

has formulae:

3. A method for inhibiting proliferation of mammalian breast cells comprising administering to a subject in need thereof a therapeutically effective amount of a compound of formula:

wherein
X¹ is C=;
L¹ is a bond;
R¹ is para to —L¹—B(OH)₂ and has formula:

(2)

n is 1;
X² is —N— or —CH—;
R³ is substituted aryl, wherein substituted aryl is and
R⁴ is substituted or unsubstituted alkyl.

* * * * *